United States Patent
Castellani

(10) Patent No.: US 7,874,426 B2
(45) Date of Patent: Jan. 25, 2011

(54) CRUSH RESISTANT NEEDLE PACKAGING ASSEMBLY HAVING RAPID NEEDLE ACCESS

(75) Inventor: Robert A. Castellani, Simpsonville, SC (US)

(73) Assignee: North American Rescue, LLC, Greer, SC (US)

( * ) Notice: Subject to any disclaimer, the term of this patent is extended or adjusted under 35 U.S.C. 154(b) by 348 days.

(21) Appl. No.: 12/009,869

(22) Filed: Jan. 23, 2008

(65) Prior Publication Data

US 2008/0173556 A1 Jul. 24, 2008

Related U.S. Application Data

(60) Provisional application No. 60/881,876, filed on Jan. 23, 2007.

(51) Int. Cl.
*B65D 81/02* (2006.01)
*A61M 5/32* (2006.01)

(52) U.S. Cl. .......... 206/365; 206/438; 206/364

(58) Field of Classification Search .......... 206/365, 206/364, 363, 210, 438, 571, 570, 804, 306; 220/367.1, 366.1, 495.11, 495.06, 495.01
See application file for complete search history.

(56) References Cited

U.S. PATENT DOCUMENTS

| | | | |
|---|---|---|---|
| 333,347 A | 12/1885 | Schrader et al. | |
| 426,400 A | 4/1890 | Tagliabue | |
| 1,280,687 A | 10/1918 | Dudley | |
| 1,667,248 A | 4/1928 | Eisele | |
| 1,803,825 A * | 5/1931 | Abernathy | 220/821 |
| 1,838,825 A | 12/1931 | Goldstein | |
| 2,400,722 A | 5/1946 | Swan | |
| 2,695,744 A * | 11/1954 | Gattuso | 229/103.11 |
| 2,935,228 A | 5/1960 | Cosby, Jr. et al. | |
| 3,114,455 A | 12/1963 | Claisse et al. | |
| 3,329,146 A | 7/1967 | Waldman, Jr. | |
| 3,934,722 A | 1/1976 | Goldberg | |
| 4,106,622 A | 8/1978 | Windischman | |
| 4,113,090 A | 9/1978 | Carstens | |
| 4,444,355 A * | 4/1984 | Cary | 229/125.13 |
| 4,592,744 A | 6/1986 | Jagger et al. | |
| 4,757,381 A * | 7/1988 | Cooper et al. | 348/66 |
| 4,877,132 A | 10/1989 | Makris et al. | |
| 4,954,239 A * | 9/1990 | Mueller | 206/571 |
| 5,161,681 A | 11/1992 | Kemp et al. | |

(Continued)

*Primary Examiner*—Mickey Yu
*Assistant Examiner*—Steven A. Reynolds
(74) *Attorney, Agent, or Firm*—McNair Law Firm, P.A.; Seann P. Lahey

(57) ABSTRACT

A rigid crush resistant plastic tube having quickly removable end caps. A hypodermic needle contained in a sterile needle wrapper is placed inside the crush resistant tube so that a portion of the wrapper is folded over the outside distal end of the tube. The end cap is then secured over the folded wrapper portion on the distal end of the tube in a friction fit arrangement to secure the needle wrapper between the cap and tube. In this arrangement, when the end cap is removed, it pulls the needle wrapper out of the protective plastic tube to allow for rapid access and deployment. In use, the plastic tubes are secured with elastic bands inside a carrying case, such as a first aid backpack. As the soft cases are often subject to substantial exterior impacts, the tubing significantly reduces the risk of needle breakage.

13 Claims, 3 Drawing Sheets

U.S. PATENT DOCUMENTS

| | | | |
|---|---|---|---|
| 5,332,092 A * | 7/1994 | Fischer | 206/365 |
| 5,417,326 A | 5/1995 | Winer | |
| 5,641,947 A * | 6/1997 | Riddle, Jr. | 177/126 |
| 5,765,682 A * | 6/1998 | Bley et al. | 206/363 |
| 6,155,420 A | 12/2000 | Phillips | |
| 6,305,541 B1 | 10/2001 | Tanner et al. | |
| 6,488,149 B1 | 12/2002 | Montagnino | |
| 6,749,601 B2 * | 6/2004 | Chin | 606/1 |
| 2007/0232978 A1 | 10/2007 | Castellani | |

* cited by examiner

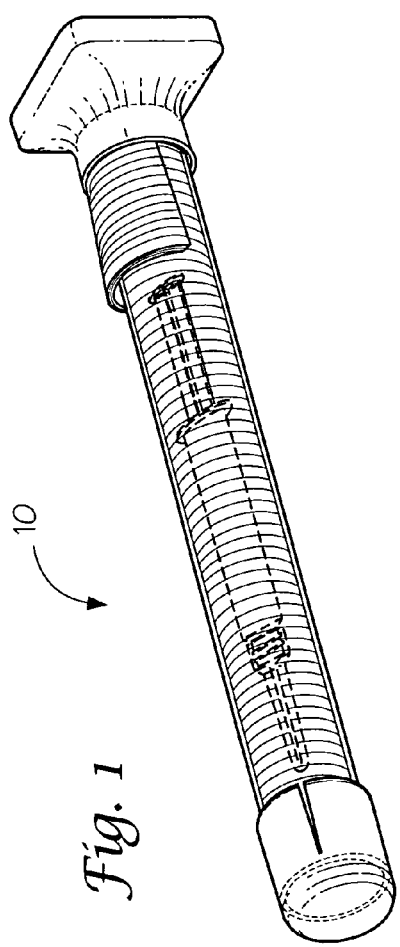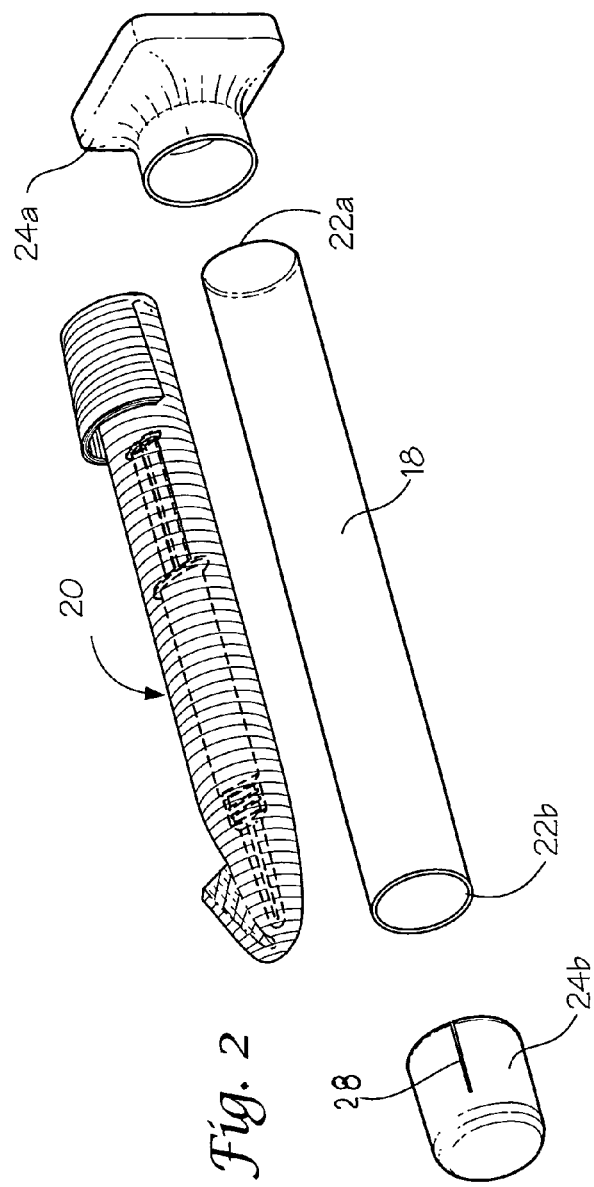

CRUSH RESISTANT NEEDLE PACKAGING ASSEMBLY HAVING RAPID NEEDLE ACCESS

CROSS REFERENCE TO RELATED APPLICATION

This application claims priority of Provisional Application Ser. No. 60/881,876, filed Jan. 23, 2007.

BACKGROUND OF THE INVENTION

1) Field of the Invention

The present invention relates to a protective packaging kit for hypodermic needles that includes a rigid crush resistant plastic tube with quickly removable end caps. The plastic tube protects against breakage during field deployment of the needles in soft cases and the end caps provide for rapid needle removal from the protective tube.

2) Description of Related Art

Combat operations by U.S. Armed Forces in various theaters around the world have lead to the establishment of mission specific combat casualty care requirements for the Department of Defense. These requirements necessitate the need to implement new and innovative casualty response training and durable precision equipment to aggressively decrease preventable combat deaths at the point of wounding in the field.

The hard lessons learned over centuries of battlefield healthcare have resulted in military guidelines for trauma management, which have mirrored tactics used in the civilian sector for many years. However, a new strategy has emerged due in large part to the life saving efforts of those in Special Operations Command, which his now being referred to as Tactical Combat Casualty Care (TCCC).

TCCC launched a total reassessment of practices under the previously established military guidelines for battlefield healthcare with the goal of decreasing preventable combat deaths at the point of wounding. Instead of the civilian-based approaches of the past, integrated strategies specific to combat realties are being required. For instance, Special Forces medics generally carry "soft" packpack type first aid kits made of durable cloth like materials that contain various essential items for dealing with life threatening wounds. These soft kits are typically subject to severe impacts associated with the rigors of warfare where the individual carrying the soft kit is often running up against walls, diving on the ground, and generally engaging in rigorous physical activity that takes a toll on the items in the kit.

Among the various items included in these soft first aid kits are decompression hypodermic needles intended for use in the management of combat casualties who present signs and symptoms of tension pneumothorax. Preliminary research data from the U.S. Arm Institute of Surgical Research has shown that needle decompression with a 14-gauge needle is as successful as a chest tube, used in the civilian sector, in relieving a tension pneumothorax and that the therapeutic benefit persists for at least four hours.

In the civilian market, such 14-gauge needles come packaged in a flexible sterile paper and plastic wrapper that does nothing to protect the needle inside except to keep it sterile. Also, because the wrappers all look the same, there is no quick way to identify different gauge needles from each other at a glance when lumped together in a first aid kit. Because the needles are usually safely contained in an ambulance, large hard shelled case, or on the shelf of a hospital supply closet, in the civilian sector this are simply not the same concerns for durability that require a protective package for the needle. Further, in civilian applications, space is often not a concern unlike in the military environment where space in the first aid kit is at a premium and a plethora of backup needles is simply not practical. Accordingly, the inclusion of decompression needles of various gauges packaged in the sterile wrapper for use in the first aid kits of military field medics resulted in broken needles due to the impacts sustained by the soft first aid kits and unnecessary delay in identifying the proper needle under combat conditions. Thus, there is a substantial need to provide a protective packaging for the decompression needles that is lightweight, extremely durable, can be operated quickly to remove the needle, and which provides a simple means of quickly identifying the proper needle.

The prior art on record at the U.S. Patent Office that discloses packaging for needles is directed to the civilian market and there are no references that deal with the concerns expressed above that are unique to the military market. For example, U.S. Pat. No. 6,305,541 (Tanner et al.) shows a combination package and needle hub assembly. An assembly of individually packaged cartridge assembles are held together in a shrink wrap, making them difficult to separate quickly. There is no discussion of indicating different needle types within the package, and the packaging is not indicated to have any particular durability for the purposes discussed above. Further, there is no teaching that the needles can be quickly removed from the containers, particularly in view of the shrink wrap.

U.S. Pat. No. 3,114,455 (Claisse et al.) show a sealed hypodermic needle package that is intended to provide sterility, but not durability. Such thin plastic tubes are easily bent and there is no discussion of the tubes have a rigid nature that would prevent damage to the needle from severe impacts.

U.S. Pat. No. 1,667,248 (Eisele) shows a tubular glass case for a thermometer. These type of enclosures are useful for simple storage in a home or hospital environment, but would be completely impractical for the military application requirements of TCCC as the glass tubing would shatter easily.

Accordingly, it is an object of the present invention to provide a protective packaging kit for decompression needles that meets the operational and durability standards of TCCC.

It is a further object of the present invention to provide a protective needle packaging kit that is lightweight to minimize added weight to the first aid kits carried by soldiers in the field.

It is a further object of the present invention to provide a protective needle packaging kit that can be operated quickly to remove the needle.

It is a further object of the present invention to provide a protective needle packaging kit that provides a simple means of quickly identifying different needle types contained in the protective packaging.

SUMMARY OF THE INVENTION

The above objectives are accomplished according to the present invention by providing a protective packaging kit consisting of a rigid crush resistant plastic tube having quickly removable end caps. The end caps are preferably made of plastic and can be color coded to indicate different needle sizes or needle products. The needle product is provided in a flexible paper and plastic wrapper that can be easily bent and broken when carried in a soft case of the type used by paramedics in the field. The hypodermic needle contained in the sterile needle wrapper is placed inside the crush resistant tube so that a portion of the wrapper is folded over the outside of the tube. The end cap is then secured over the folded wrapper portion on the distal end of the tube in a friction fit arrangement to secure the needle wrapper between the cap and tube. In this arrangement, when the end cap is removed, it pulls the needle wrapper out of the protective plastic tube to allow for rapid access and deployment. In use, the plastic tubes are secured with elastic bands inside a carrying case, such as a first aid backpack. As the soft cases are often subject to substantial exterior impacts, the tubing significantly reduces the risk of needle breakage.

In particular, the present invention is directed towards a protective needle packaging assembly comprising a hypodermic needle contained in a wrapper, wherein the wrapper includes an extended tab for providing a gripping area to open the wrapper to retrieve the needle; a rigid protective tube for receiving the needle in the wrapper, wherein the extended tab is folded over an open first distal end of the tube and carried adjacent to an exterior side of the tube; and, an end cap mounted to the first distal end so that at least a portion of the extended tab is positioned between the end cap and the exterior side of the tube in a friction fit engagement with the end cap; whereby removal of the end cap causes the extended tab to be withdrawn with the end cap so that the wrapper is simultaneously withdrawn from the rigid protective tube in a single opening motion to allow for quick access to the hypodermic needle.

In a further embodiment, the rigid protective tube is constructed of a clear and transparent material for viewing the wrapper through the tube.

In a further embodiment, the end cap includes a bulbous grip portion to promote ease of removal from the first distal end of the tube.

In a further embodiment, the end cap includes a tube receiving opening having a diameter greater than a diameter of the tube, wherein the end cap fits loosely over the first distal end of the tube to accommodate insertion of the extended tab between the end cap and the exterior side of the tube.

In a further embodiment, the end cap includes a release slit extending from a tube receiving opening end along a side wall generally towards an enclosed cover end, wherein the release slit is carried adjacent the exterior side of the tube when mounted on the tube to resist vacuum lock between the end cap and the tube.

In a further embodiment, the end cap is color coded to a pre-selected hypodermic needle so that a given hypodermic needle carried in the tube can be identified by the color of the end cap.

In a further embodiment, a shape of the end cap is coded to a pre-selected hypodermic needle so that a given hypodermic needle carried in the tube can be identified by the shape of the end cap.

BRIEF DESCRIPTION OF THE DRAWINGS

The construction designed to carry out the invention will hereinafter be described, together with other features thereof. The invention will be more readily understood from a reading of the following specification and by reference to the accompanying drawings forming a part thereof, wherein an example of the invention is shown and wherein:

FIG. 1 shows a perspective view of the needle packaging assembly according to the present invention;

FIG. 2 shows an exploded view of the needle packaging assembly according to the present invention;

DETAILED DESCRIPTION OF A PREFERRED EMBODIMENT

Figure 8:
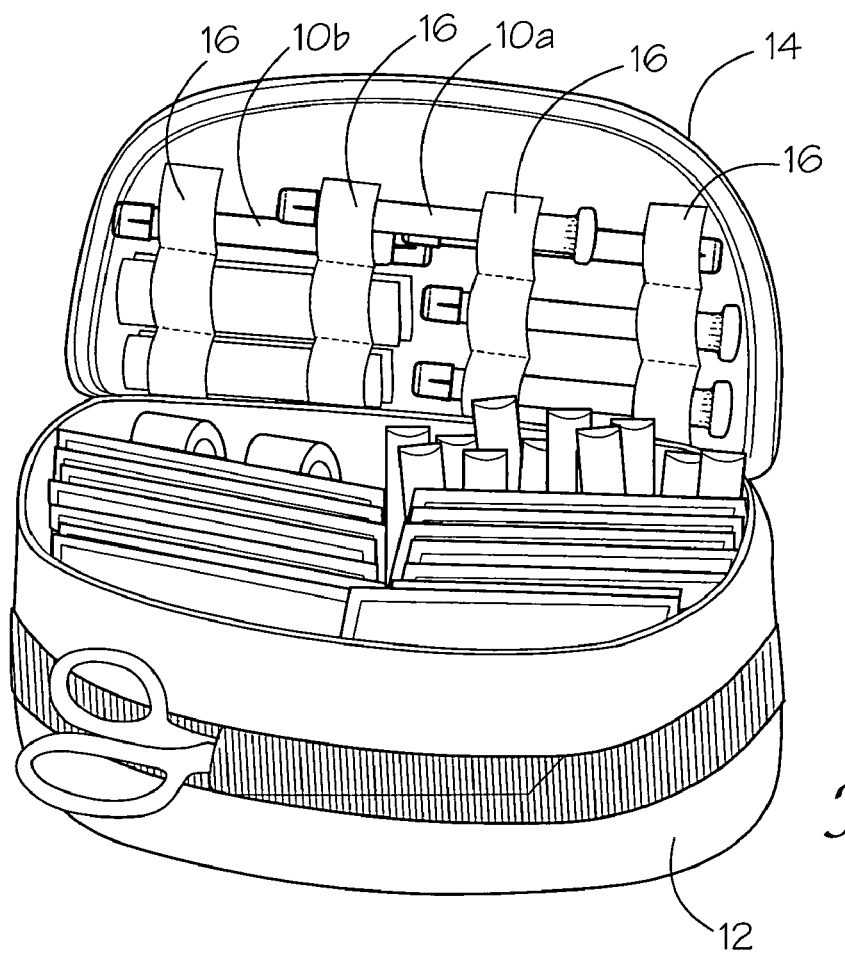

With reference to the drawings, the invention will now be described in more detail. Referring to FIG. 1, a protective needle packaging kit, designated generally as 10, is shown in a completely assembled form for insertion into a first aid kit of the type having a soft case covering. Because the soft case cannot protect the needles from severe impacts that would damage the needles, protective needle packaging kit 10 is required to maintain viability of the needles during combat operations in the field. Referring to FIG. 8, a soft first aid kit 12 is shown having a lid 14 that contains a series of straps 16 for securing medical items. In particular, a pair of hypodermic needles are provided in protective needle packaging kits 10a and 10b, which are secured by straps 16 to the inside of lid 14. In this arrangement, it is clear to see how pressure on the top of lid 14 would snap an unprotected hypodermic needle, which is fairly fragile and easily broken in such a storage environment if not adequately shielded. Preferably, straps 16 are constructed of a stretchable material to allow for easy insertion and removal of needle packaging kits 10a and 10b, while also holding them securing in place.

Referring to FIG. 2, protective needle packaging kit 10 includes a rigid crush resistant plastic tube 18. This tube is generally inflexible and made of lightweight durable clear and transparent plastic material. The clear plastic help to identify the enclosed hypodermic needle in instances where needles of various type or gauge are included in a single first aid kit. The tubing must be open at one end to allow insertion of the hypodermic needle in its sterile paper and plastic wrapper, designated generally as 20. In the illustrated embodiment, tube 18 is open at both distal ends 22a and 22b to simplify and reduce manufacturing costs.

Figure 5:
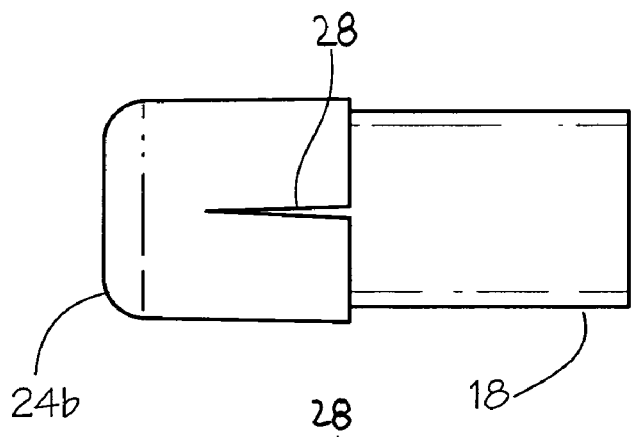
FIG. 5 shows a detailed side view of an alternative end cap according to the present invention.
Figure 6:
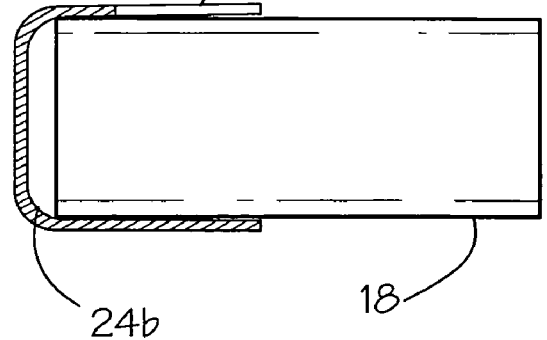
FIG. 6 shows a cross-section view of the alternative end cap in FIG. 5 according to the present invention.
Figure 7:
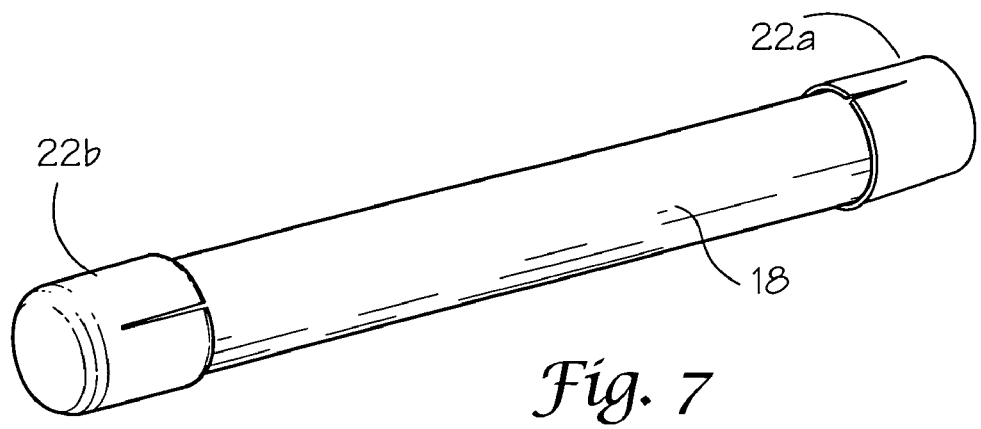
FIG. 7 shows a perspective view of an alternative embodiment for the end caps according to the present invention; and, FIG. 8 shows a perspective view of the needle packaging assembly as secured in a first aid kit according to the present invention.

Continuing to refer to FIG. 2, a pair of end caps 24a and 24b are provided which are adapted to be inserted over each of distal ends 22a and 22b of tube 18. In the preferred embodiment, end caps 24a and 24b are different in appearance to identify one as being the end cap to remove to access the needle therein. The end caps are preferably made of lightweight plastic or rubber and can be color coded and/or shape coded to indicate different needle sizes or needle products. In the preferred embodiment of FIG. 2, end cap 24a is preferably colored red and is shaped to have a bulbous arrangement to promote griping and removal from distal end 22a of tube 18. To the contrary, end cap 24b is black with no bulbous shape and is generally form fitting over distal end 22b. Referring to FIG. 7, an alternative embodiment is shown in which both end caps 24a and 24b would be black in color to indicate a different needle product from the embodiment represented in FIG. 2. Further, in the preferred embodiment, end cap 24a is adapted to be quickly removable from distal end 22a of tube 18 to promote ease of access to the needle contained therein. This can be accomplished by forming end cap 24a to fit in a slightly loose arrangement over distal end 22a or 22b of tube 18, or by placing a release slit 28 (best shown in FIGS. 5 and 6) in the side of end cap 24a to prevent vacuum lock between the cap and tube 18. Release slit 28 can be formed in either or both of end caps 24a and 24b, as shown in FIG. 5. Release slit 28 extends from a tube receiving opening end along a side wall generally towards an enclosed cover end of the end caps. Release slit 28 is carried adjacent the exterior side of said tube when mounted on the tube to resist vacuum lock between the end cap and the tube. Further, end caps 24a and 24b include a tube receiving opening having a diameter greater than a diameter of said tube, wherein the end caps 24a and 24b fit loosely over the distal ends of the tube to accommodate insertion of extended tab 26 between a selected end cap and the exterior side of the tube. By forming end cap 24a in a loosely fitted arrangement with distal end 22a, there is room to accommodate extended tab 26 between the end cap and exterior side of the tube. The preferred embodiment for making end cap 24a quickly removable, however, is described herein below as it relates to a folder extended tab 26 portion of the needle wrapper between tube 18 and end cap 24a.

Figure 3:
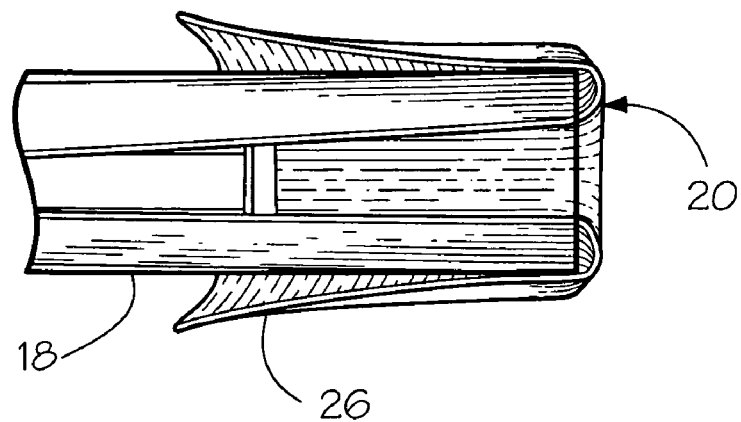
FIG. 3 shows a detailed side view of one end of the protective tube with the needle wrapper extended tab folded over the distal end of the tube according to the present invention.
Figure 4:
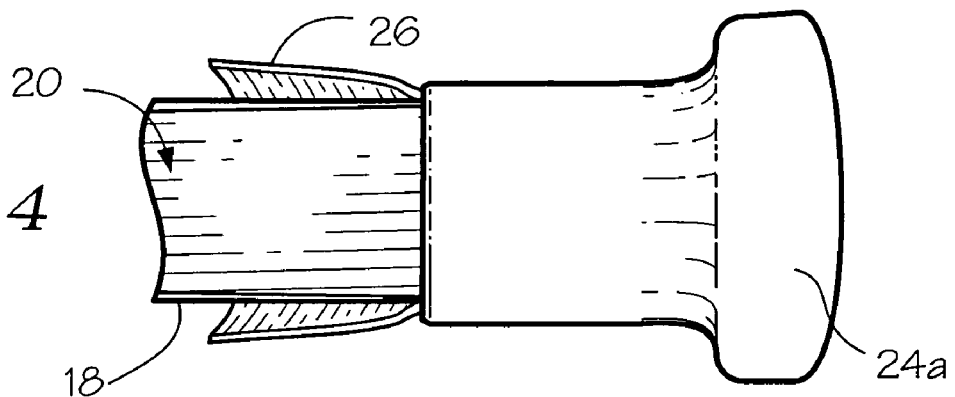
FIG. 4 shows a detailed side view of the end cap secured over the needle wrapper extended tab on the distal end of the tube according to the present invention.

Referring to FIGS. 3 and 4, a needle product, which in the illustrated application is an IV catheter 14 gauge hypodermic needle, is provided in flexible paper and plastic sterile wrapper 20 for use in chest decompression. As detailed above, this does not provide protection for the needle therein from being easily bent and broken when carried in a soft case 12 of the type used by paramedics in the field. Needle wrapper 20 includes an extended tab 26 that provides a grip portion used to pry the plastic layer from the paper backing to gain access to the needle inside. The needle wrapper 20 is placed within rigid tube 18 so that a portion of extended tab 26 is folded over the outside of distal end 22a of tube 18 and positioned adjacent the exterior side of tube 18.

Referring to FIG. 4, once extended tab 26 is positioned as in FIG. 3, end cap 24a is secured over the folded portion of extended tab 26 in a friction fit arrangement to secure the needle within tube 18 and provide engagement between end cap 24a and extended tab 26. In this arrangement, when end cap 24a is removed, the friction fit is sufficient to pull needle wrapper 20 out of rigid tube 18 in a single opening motion to allow for rapid access and deployment of the hypodermic needle therein. Thus, the needle is removed from the protective tubing through the single motion of removing the end cap, which saves time that may be critical in saving lives so that the medic does not have to fumble with attempting to remove the needle wrapper from the protective tube.

While a preferred embodiment of the invention has been described using specific terms, such description is for illustrative purposes only, and it is to be understood that changes and variations may be made without departing from the spirit or scope of the following claims.

What is claimed is:

1. A protective needle packaging assembly comprising:
   a hypodermic needle contained in a wrapper, wherein said wrapper includes an extended tab for providing a gripping area to open the wrapper to retrieve said needle;
   a rigid protective tube for receiving said needle in said wrapper, wherein said extended tab is folded over an open first distal end of said tube and carried adjacent to an exterior side of said tube; and,
   an end cap mounted to said first distal end so that at least a portion of said extended tab is positioned between said end cap and said exterior side of said tube in a friction fit engagement with said end cap;
   whereby removal of said end cap causes said extended tab to be withdrawn with said end cap so that said wrapper is simultaneously withdrawn from said rigid protective tube in a single opening motion to allow for quick access to said hypodermic needle.

2. The needle packaging assembly of claim 1 wherein said rigid protective tube is constructed of a clear and transparent material for viewing said wrapper through said tube.

3. The needle packaging assembly of claim 1 wherein said end cap includes a bulbous grip portion to promote ease of removal from said first distal end of said tube.

4. The needle packaging assembly of claim 1 wherein said end cap includes a tube receiving opening having a diameter greater than a diameter of said tube, wherein said end cap fits loosely over said first distal end of said tube to accommodate insertion of said extended tab between said end cap and said exterior side of said tube.

5. The needle packaging assembly of claim 1 wherein said end cap includes a release slit extending from a tube receiving opening end along a side wall generally towards an enclosed cover end, wherein said release slit is carried adjacent said exterior side of said tube when mounted on said tube to resist vacuum lock between said end cap and said tube.

6. The needle packaging assembly of claim 1 wherein said end cap is color coded to a pre-selected hypodermic needle so that a given hypodermic needle carried in said tube can be identified by said color of said end cap.

7. The needle packaging assembly of claim 1 wherein a shape of said end cap is coded to a pre-selected hypodermic needle so that a given hypodermic needle carried in said tube can be identified by said shape of said end cap.

8. A protective needle packaging assembly comprising:
   a hypodermic chest decompression needle;
   a flexible wrapper enclosing said needle in a sterile package;
   an extended tab carried at a distal end of said flexible wrapper for providing a gripping area to open said wrapper and retrieve said needle;
   a generally inflexible protective tube constructed of a clear and transparent plastic material and having an open first distal end and an open second distal end, wherein said flexible wrapper is carried in said protective tube to resist deformation of said chest decompression needle;
   said extended tab being folded over said open first distal end to extend from an interior side of said protective tube to an exterior side of said tube so that said extended tab is arranged to extend along a portion of said exterior side of said tube;
   a first end cap carried by said open first distal end, wherein said extended tab is disposed between said first end cap and said exterior side of said tube so that said extended tab is secured to said first end cap in a friction fit arrangement;
   a second end cap carried by said open second distal end to enclose said protective tube together with said first end cap; and,
   a release slit included in at least one of said first end cap and said second end cap carried adjacent said exterior side of said tube to resist vacuum lock between said end caps and said tube;
   whereby removal of said first end cap causes said extended tab to be withdrawn with said first end cap so that said wrapper is simultaneously withdrawn from said protective tube in a single opening motion to allow for quick access to said needle.

9. The needle packaging assembly of claim 8 wherein said first end cap includes a bulbous grip portion to promote ease of removal from said open first distal end of said tube.

10. The needle packaging assembly of claim 8 wherein said first end cap includes a tube receiving opening having a diameter greater than a diameter of said tube, wherein said first end cap fits loosely over said first distal end of said tube to accommodate insertion of said extended tab between said first end cap and said exterior side of said tube.

11. The needle packaging assembly of claim 8 wherein release slit extends from a tube receiving opening end of said end cap along a side wall generally towards an enclosed cover end of said end cap.

12. The needle packaging assembly of claim 8 wherein at least one of said first end cap and said second end cap is color coded to a pre-selected hypodermic needle so that a given hypodermic needle carried in said tube can be identified by said color of said end cap.

13. The needle packaging assembly of claim 8 wherein a shape of at least one of said first end cap and said second end cap is coded to a pre-selected hypodermic needle so that a given hypodermic needle carried in said tube can be identified by said shape of said end cap.

* * * * *